United States Patent [19]

Miller et al.

[11] 4,366,165
[45] Dec. 28, 1982

[54] 1 AND 4-ARYLCYANOALKYL-1,2,4-TRIAZOLES AND FUNGICIDAL USE

[75] Inventors: George A. Miller, Maple Glen; Hak-Foon Chan, Doylestown, both of Pa.

[73] Assignee: Rohm and Haas Company, Philadelphia, Pa.

[21] Appl. No.: 233,366

[22] Filed: Feb. 11, 1981

Related U.S. Application Data

[63] Continuation-in-part of Ser. No. 798,286, May 19, 1977, abandoned.

[51] Int. Cl.$^3$ ............... A01N 43/64; A01N 59/16; C07D 249/08; C07F 3/06
[52] U.S. Cl. ............... 424/269; 260/456 R; 260/465 E; 260/465 F; 260/465 G; 260/465 H; 260/465 K; 260/465 R; 548/101; 548/262; 564/249
[58] Field of Search ............... 548/262, 101; 424/269, 424/245

[56] References Cited

U.S. PATENT DOCUMENTS

| | | | |
|---|---|---|---|
| 3,821,394 | 6/1974 | Timmler et al. | 424/273 |
| 3,897,438 | 7/1975 | Draber et al. | 548/345 |
| 4,005,083 | 1/1977 | Buchel et al. | 548/101 |
| 4,073,921 | 2/1978 | Miller et al. | 548/336 |

FOREIGN PATENT DOCUMENTS

2821971  5/1977  Fed. Rep. of Germany ...... 424/269

*Primary Examiner*—Alton D. Rollins
*Attorney, Agent, or Firm*—Alex R. Sluzas

[57] ABSTRACT

This invention relates to 1 and 4-arylcyanoalkyl-1,2,4-triazoles, their enantiomorphs, and acid addition salts and metal salt complexes. This invention also relates to the method of preparation and use of these compounds. These compounds enantiomorphs, salts and complexes are highly active broad-spectrum systemic fungicides effective in controlling phytopathogenic fungi such as barley net blotch (*Helminthosporium teres*), grey mold (*Botrytis cinerea*), bean powdery mildew (*Erysiphe polygoni*), grape downy mildew (*Plasmopora viticola*), rice blast (*Piricularia oryzae*), tomato late blight (*Phytophthora infestans*) and wheat stem rust (*Puccinia graminis f. sp. tritici* race 15B-2).

10 Claims, No Drawings

1 AND 4-ARYLCYANOALKYL-1,2,4-TRIAZOLES AND FUNGICIDAL USE

SUMMARY OF THE INVENTION

This application is a continuation-in-part application of U.S. Ser. No. 798,286 filed May 19, 1977, abandoned. This invention relates to compounds of the formula

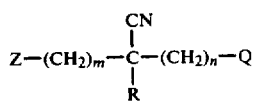

wherein Z is an aryl group or a substituted aryl group; R is a hydrogen atom, an alkyl group, a cycloalkyl group, an alkenyl group, a cycloalkenyl group, an alkynyl group, an aryl or substituted aryl group, an aralkyl or substituted aralkyl group, an alkoxy group, an alkenoxy group, an alkynoxy group, an aryloxy or substituted aryloxy group, an aralkoxy or substituted aralkoxy group, or a hydroxy group; Q is a 1-(1,2,4-triazolyl) or a 4-(1,2,4-triazolyl), m is zero or the integer 1; n is the integer 1 or 2; and the agronomically acceptable enantiomorphs, acid addition salts and metal complexes thereof.

DETAILED DESCRIPTION OF THE INVENTION

This invention relates to novel 1 & 4-acrylcyanoalkyl-1,2,4-triazoles and the enantiomorphs, acid addition salts and metal salt complexes thereof, as well as their method of preparation and their use as highly active broad-spectrum systemic fungicides. In particular, this invention relates to compounds of the formula

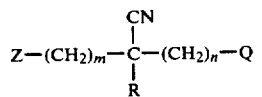

wherein Z is an optionally substituted ($C_6$ to $C_{10}$) aryl group; R is a hydrogen atom, a ($C_1$ to $C_{12}$) alkyl group, a ($C_3$ to $C_8$) cycloalkyl group, a ($C_2$ to $C_8$) alkenyl group, a ($C_5$ to $C_8$) cycloalkenyl group, a ($C_2$ to $C_8$) alkynyl group, an optionally substituted ($C_6$ to $C_{10}$) aryl group, an optionally substituted ($C_7$ to $C_{14}$) aralkyl group, a ($C_1$ to $C_4$) alkoxy group, a ($C_2$ to $C_4$) alkenoxy group, a ($C_2$ to $C_4$) alkynoxy group, an optionally substituted ($C_6$ to $C_{10}$) aryloxy group, an optionally substituted ($C_7$ to $C_{14}$) aralkoxy group or a hydroxy group; Q is an optionally substituted 1-(1,2,4-triazolyl) or 4-(1,2,4-triazolyl); m is zero or the integer 1; n is the integer 1 or 2; and the agronomically acceptable enantiomorphs, acid addition salts and metal salt complexes thereof.

By the term "aryl," as used in defining the substituents Z and R in the present specification and claims, is meant an aromatic ring structure of from 6 to 10 carbon atoms, preferably a phenyl or naphthyl group which is optionally substituted with up to three substituents, preferably with up to two substituents selected from the group consisting of halogen, nitro, trihalomethyl, cyano, ($C_1$ to $C_4$) alkyl, ($C_1$ to $C_4$) alkoxy, ($C_1$ to $C_4$) alkylthio, ($C_1$ to $C_4$) alkylsulfinyl and ($C_1$ to $C_4$) alkylsulfonyl.

Typical aryl substituents encompassed in this invention are phenyl, naphthyl, 4-chlorophenyl, 2,4-dibromophenyl, 3,5-difluorophenyl, 2,4,6-trichlorophenyl, 2,3,5-tribromophenyl, 3,4-dichlorophenyl, 2-chloro-4-iodophenyl, 3-chloro-4-nitrophenyl, 2,4-dinitrophenyl, 3,4,5-trimethylphenyl, 2-nitro-4-methoxyphenyl, 2-chloronaphthyl, 2-nitronaphthyl, 2,4-dimethoxyphenyl, 4-trifluoromethylphenyl, 2-nitro-4-trifluoromethylphenyl, 3,5-dimethylthiophenyl, 2-cyano-5-methylphenyl, 2,4-dimethylsulfinylphenyl, 2,4-dimethylsulfonylphenyl, 2,4-diiodonaphtyl, 2-iodo-4-methylphenyl and the like.

The term "aralkyl" is used, in defining the substituent R in the present specification and claims, to define an aralkyl group wherein the alkyl chain is from 1 to 4 carbon atoms and can be branched or straight chained and the aryl portion of the group is meant to be defined as above. Typical aralkyl substituents encompassed in this invention are 2,4-dichlorobenzyl, 2,4-dibromobenzyl, 2,5-dinitrobenzyl, 2,4,6-trichlorobenzyl, 3,5-dimethoxyphenethyl, 2,5-dimethylthiophenylpropyl, 2,4-diiodophenyl-2-methyl-propyl, 3,4-dimethylsulfinylbenzyl, 2,3-dimethylsulfonylphenylethyl, 2,4,5-trimethylphenylbutyl, 2,4-dicyanonaphthylmethyl, 2-nitronaphthylethyl, 2-nitronaphthylpropyl, 2,4-dibromonaphthylbutyl and the like.

The term "alkyl," as utilized in defining the substituent R in the present specification and claims, is meant to include both branched and straight chained alkyl groups of from 1 to 12 carbon atoms. Typical alkyl groups which are encompassed by the use of this term in defining this invention are methyl, ethyl, propyl, isopropyl, n-butyl, sec-butyl, iso-butyl, tert-butyl, pentyl, neopentyl, iso-pentyl, hexyl, heptyl, iso-octyl, nonyl, decyl, iso-decyl, undecyl, dodecyl and the like.

In the definition of Q, as used in the specification and claims, the term "optionally substituted 1-(1,2,4-triazolyl) or 4-(1,2,4-triazolyl)" is meant to include unsubstituted 1 & 4-(1,2,4-triazolyl) and 1 & 4-(1,2,4-triazolyl) which can be substituted with up to two substitutes selected from the group consisting of halogen, ($C_1$ to $C_4$) alkyl, nitro and cyano.

The acids which can be utilized in making the acid addition salts of the present invention include hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric, phthalic and the like.

Another embodiment of this invention is the metal salt complexes of the formula

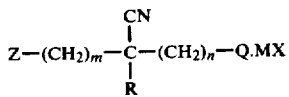

wherein Z, R, Q, m and n are as defined in Formula (II) above and M is a cation selected from Group IIA, IB, IIB, VIB, VIIB, and VIII of the Periodic Table and X is an anion counterion selected in such a manner that the sum of the valence charges of the cation M and anion X equal zero.

Typical cations encompassed by this invention are magnesium, manganese, copper, nickel, zinc, iron, cobalt, calcium, tin, cadmium, mercury, chromium, lead, barium and the like.

Typical anions encompassed by this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, (mono) or (di) ($C_1$ to $C_4$) alkyldithiocarbamate, ($C_1$ to $C_4$) alkylene-bisdithiocarbamate, and the like.

A preferred embodiment of this invention is the compounds, enantiomorphs, salts and complexes of Formulas (II) and (III) wherein Z is a phenyl or naphthyl group preferably a phenyl group optionally substituted with up to three substituents preferably with up to two substituents selected from the group consisting of halogen, nitro, trihalomethyl, cyano, ($C_1$ to $C_4$) alkyl, ($C_1$ to $C_4$) alkyl, ($C_1$ to $C_4$) alkoxy, ($C_1$ to $C_4$) alkylthio, ($C_1$ to $C_4$) alkylsulfinyl and ($C_1$ to $C_4$) alkylsulfonyl; R is selected from the group consisting of ($C_1$ to $C_{12}$) alkyl, ($C_5$ to $C_7$) cycloalkyl, ($C_2$ to $C_4$) alkenyl, ($C_5$ to $C_6$) cycloalkenyl, ($C_2$ to $C_4$) alkynyl, unsubstituted phenyl, benzyl or phenethyl or phenyl, benzyl or phenethyl, the aromatic portion of which is substituted with up to two halogen atoms; Q is an unsubstituted 1 or 4-(1,2,4-triazole); m is zero; and n is the inter 1.

A more preferred embodiment of this invention is the compounds, enantiomorphs, salts and complexes of Formulas (II) and (III) wherein Z is phenyl optionally substituted with up to three substituents preferably with up to two substituents selected from the group consisting of chlorine, bromine, methyl, methoxy, nitro and methylthio; R is ($C_1$ to $C_{12}$) alkyl, cyclohexenyl, propargyl, phenyl, benzyl or phenethyl or monochloro substituted phenyl, benzyl or phenethyl; Q is an unsubstituted 1 or 4-(1,2,4-triazole); m is zero; and n is the inter 1.

Typical compounds encompassed by the present invention include:

1-[β-cyano-β-(2,4-dibromophenyl)hexyl]1,2,4-triazole
4-[β-cyano-β-(2,5-dinitrophenyl)octyl]1,2,4-triazole
1-[β-cyano-α-(3,5-ditrifluoromethylphenyl)nonyl]1,2,4-triazole
4-[β-cyano-δ-(2,4,6-trichlorophenyl)dodecyl]1,2,4-triazole
1-[β-cyano-β-(2,4,5-trimethylphenyl)tetradecyl]1,2,4-triazole
4-[β-cyano-β-(2,4-dimethoxyphenyl)hexyl]3-methyl-1,2,4-triazole
1-[β-cyano-β-(2,4-dimethylthiophenyl)hexyl]5-chloro-1,2,4-triazole
4-[β-cyano-β-(3-iodophenyl)decyl]1,2,4-triazole
1-[β-cyano-β-(2,6-dichlorophenyl)pentyl]1,2,4-triazole
4-[β-cyano-β-(3,5-diethylphenyl)buten-2-yl]1,2,4-triazole
1-[β-cyano-β-(4-methylsulfonylphenyl)butyn-2-yl]1,2,4-triazole
4-[β-cyano-β-(4-cyanophenyl)propyl]1,2,4-triazole
1-[β-cyano-γ-(2,4-dichlorobenzyl)heptyl]1,2,4-triazole
4-[β-cyano-β-(2,4-difluorobenzyl)octyl]1,2,4-triazole
1-[β-cyano-β-(2,4-dichlorophenethyl)hexyl]1,2,4-triazole
4-[β-cyano-β-(4-iodophenyl)undecyl]1,2,4-triazole
1-[β-cyano-δ-(2-methyl-4-chlorophenyl)dodecyl]1,2,4-triazole
4-[β-cyano-δ-(2-methyl-4-methylthiophenyl)tridecyl]1,2,4-triazole
1-[β-cyano-β-(4-tolyl)hexyl]1,2,4-triazole
4-[β-cyano-β-(4-anisyl)hexyl]1,2,4-triazole
4-[β-cyano-β-(2,4-dichlorophenyl)-β-cyclopropylethyl]1,2,4-triazole
4-[β-cyano-β-(2,4-dichlorophenyl)-β-cyclopentylethyl]1,2,4-triazole
1-[β-cyano-β-(2,4-dichloronaphthyl)hexyl]1,2,4-triazole
4-[β-cyano-β-(2-fluoronaphthyl)hexyl]1,2,4-triazole
1-[β-cyano-β-(2-nitronaphthyl)hexyl]1,2,4-triazole
4-[β-cyano-β-(3,4-dichlorophenyl)octyl]1,2,4-triazole
1-[β-cyano-β-(2,3-difluorophenyl)propyl]1,2,4-triazole
4-[β-cyano-β-(2,5-diethylphenyl)tetradecyl]1,2,4-triazole
1-[β-cyano-γ-(2,3,5-trichlorophenyl)hexyl]1,2,4-triazole
4-[β-cyano-β-(4-trichloromethylphenyl)pentyl]1,2,4-triazole
1-[β-cyano-β-(4-ethylsulfonylphenyl)hexyl]5-cyano-1,2,4-triazole
4-[β-cyano-β-(2-bromo-4-nitrophenyl)hexyl]3-bromo-1,2,4-triazole
1-[β-cyano-β-(3-methylsulfinylphenyl)butyl]3-ethyl-1,2,4-triazole
4-[β-cyano-β-(2-methoxynaphthylethyl)hexyl]1,2,4-triazole
1-[β-cyano-β-(2,4-dichlorophenyl)-4-chlorophenethyl]1,2,4-triazole
4-[β-cyano-β-(4-chlorophenyl)-4-chlorophenethyl]1,2,4-triazole
1-[β-cyano-γ-(3,5-dinitrophenyl)hexyl]1,2,4-triazole and the agronomically acceptable enantiomorphs, acid addition salts and metal salt complexes thereof.

The 1 & 4-arylcyanoalkyl-1,2,4-triazoles of the present invention can be prepared by standard general synthetic routes. A preferred method for preparing the 1-arylcyanoalkyl-1,2,4-triazoles of this invention is as follows:

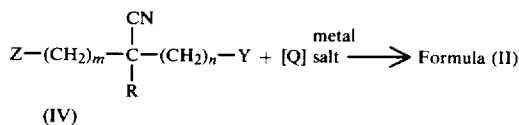

In this reaction sequence Z, R, Q, m and n are as defined in Formula (II); Y is halide, alkanesulfonate, arylsulfonate and the like and the metal salt of the 1-(1,2,4-triazole), Q, is preferably a sodium or potassium salt. This reaction can be run either neat or in an appropriate solvent such as benzene, toluene, xylene, glyme, N,N-dimethylformamide, dimethylsulfoxide and the like, at temperatures from about 0° C. to about 150° C.

When the starting material of Formula (IV) is reacted with the 1H-1,2,4-triazole free base instead of its metal salt, at temperatures from about 50° C. to about 180° C. a mixture of 1-substituted and 4-substituted 1,2,4-triazoles is obtained and these triazoles can be easily separated by conventional chemical spearation techniques such as extraction, chromatography, crystallization and the like.

A preferred method for preparing the 4-arylcyanoalkyl-1,2,4-triazoles of this invention is as follows:

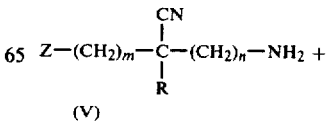

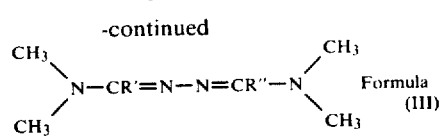

Formula (III)

In this reaction sequence Z, R, m and n are as defined in Formula (II) and R' and R" are independently a gydrogen atom, a halogen atom, a ($C_1$ to $C_4$) alkyl group, a nitro group or a cyano group. This reaction is run in an appropriate inert solvent such as benzene, toluene, xylene, and the like at temperatures from about 0° C. to about 150° C. with or without the presence of a suitable catalyst such as p-toluenesulfonic acid, benzene sulfonic acid, methanesulfonic acid and the like. Either reactant i.e. Formula (V) or (VI) can be used in excess in this preparation and the mode of addition is not critical.

The starting materials of Formula (IV) can be prepared by standard synthetic methods. Examples of such preparative methods can be found in U.S. patent application Ser. No. 557,546 filed Mar. 12, 1975 by George A. Miller et al., now abandoned, which is assigned to a common assignee.

The starting materials of Formula (V) can be prepared by making the corresponding Formula (IV) starting materials wherein Y is chlorine, bromine and the like and reacting them with ammonia, either neat or in an appropriate solvent such as diethyl ether, tetrahydrofuran, methanol and the like at temperatures from about −40° C. to about 100° C.

The acid addition salts of the 1 & 4-arylcyanoalkyl-1,2,4-triazoles of this invention can be prepared by standard techniques well-known in the art. For example, the 1 or 4-arylcyanoalkyl-1,2,4-triazole of Formula (II) can be dissolved in an appropriate solvent such as diethyl ether, tetrahydrofuran, ethanol, methanol, and the like or combinations thereof, and treated with an equivalent or excess amount of a mineral or organic acid which may or may not be dissolved in an appropriate solvent. The mixture is then either cooled or evaporated to give the salt which can either be used as such or recrystallized from an appropriate solvent or combination of appropriate solvents.

The metal salt complexes of the above 1 & 4-substituted arylcyanoalkyl-1,2,4-triazoles can be prepared by adding dropwise, with stirring, a stoichiometric amount of a metal salt dissolved in an appropriate solvent or combination of solvents to a solution of the 1 & 4-substituted arylcyanoalkyl 1,2,4-triazole of Formula (II) dissolved in a similarly appropriate solvent or combination of solvents. The reaction mixture is briefly stirred and the solvent is removed under reduced pressure to give the metal salt complex of the respective 1 & 4-substituted arylcyanoalkyl-1,2,4-triazoles of Formula (III).

The metal salt complexes can also be prepared by mixing stoichiometric or excess amounts of the metal salt and a 1 & 4-substituted arylcyanoalkyl-1,2,4-triazole of Formula (II) in the desired amount of solvent containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications.

Solvents that can be utilized in these procedures include any polar solvent e.g., water, methanol, ethanol, isopropanol or ethylene glycol and any aprotic dipolar solvent e.g., dimethylsulfoxide, acetonitrile, dimethylformamide, nitromethane or acetone.

The metal salt cations that can be used in these procedures can be selected from the group consisting of calcium, magnesium, manganese, copper, nickel, zinc, iron, cobalt, tin, cadmium, mercury, chromium, lead, barium and the like.

Any appropriate anion e.g., chloride, bromide, iodide, sulfate, bisulfate, phosphate, nitrate, perchlorate, carbonate, bicarbonate, hydrosulfide, hydroxide, acetate, oxalate, malate, citrate and the like may be utilized as the counterion in the metal salt.

Any metal containing fungicides can also act as safening agents when used in place of metal salts. Typical metal containing fungicides that can be utilized in these procedures are: (a) dithiocarbamates and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb); (b) copper-based fungicides such as cuprous oxide, copper oxychloride, copper naphthenate, and Bordeaux mixture; and (c) miscellaneous fungicides such as: phenylmercuric acetate, N-ethylmercuri-1,2,3,6-tetrahydro-3,6-endomethano-3,4,5,6,7,7-hexachlorophthalimide, phenylmercuri monoethanolammonium lactate, nickel-containing compounds and calcium cyanamide.

The compounds of this invention possess an asymmetric carbon atom and thus exit as racemic mixtures. The d and l enantiomorphs in these racemic mixtures can be separated via standard techniques such as fractional crystallization with d-tartaric acid, l-tartaric acid, l-quinic acid and the like followed by basification and extraction of the d or l enantiomorph free base.

The following examples are provided merely to illustrate the methods of preparation of the compounds of the present invention. These examples are not meant to be considered, in any way, as limitations of the breadth and scope of the present invention. The temperatures expressed in these examples are in degrees centigrade.

EXAMPLE 1

4-[2-Cyano-2-(2,4-dichlorophenyl)hexyl]-1,2,4-triazole

A mixture of 12 g (0.036 mole) of 2-cyano-2-(2,4-dichlorophenyl)hexyl bromide and 10 g (0.145 mole) of 1H-1,2,4-triazole is heated at 185° overnight. The reaction is cooled and poured into water and extracted with ether. When the combined ether extracts are washed with water, white precipitate separate from the ether layer. This precipitate is filtered and dried in vacuum to give 1 g of a white solid, mp 46°–9°. Glc and nmr analysis reveal this material to be 4-[2-cyano-2-(2,4-dichlorophenyl) hexyl]-1,2,4-triazole.

nmr (CDCl$_3$): δ0.7–3.2 (complex multiplets, 9H), 5.0 (q, 2H), 7.2–7.8 (m, 3H), 8.15 (s, 2H).

EXAMPLE 2

1-[2-Cyano-2-(2,4-dichlorophenyl)hexyl]-1,2,4-triazolium nitrate and
4-[2-cyano-2-(2,4-dichlorophenyl)hexyl]-1,2,4-triazolium nitrate To the ether filtrate from the above experiment is added conc. nitric acid dropwise until solution becomes strongly acidic. The white precipitate formed is triturated several times with ether/hexane mixture and then collected by filtration to give 2 g of product, mp 110°-120°. Glc and nmr analysis reveal that this material is a mixture of 1-[2-cyano-2-(2,4-dichlorophenyl)-hexyl]-1,2,4-triazolium nitrate and 4-[2-cyano-2-(2,4-dichlorophenyl) hexyl]-1,2,4-triazolium nitrate in a 2:1 ratio.

nmr (DMSO): δ0.6–3.0 (m, 9H), 5.1 (q, 2H), 7.3–7.8 (m, 3H), singlets at 8.1, 8.7, 9.2 integrated for 2H, 14.2 (s, 1H).

EXAMPLE 3

Preparation of 1-[2-Cyano-2-(2,4-dichlorophenyl)hexyl]-1,2,4-triazolium nitrate

A. 2-Cyano-2-(2,4-dichlorophenyl)hexyl bromide

A solution containing 1.0 mole of n-butyl bromide and 1.0 mole of 2,4-dichlorophenyl cyanide in 250 ml of methylene chloride is added into a 25% aqueous solution of sodium hydroxide (500 ml) with 5.0 g of tetraethylammonium bromide. The reaction mixture is stirred vigorously under reflux for 3 hours to give 90% yield of desired product which is shown to be 90% pure by glc analysis and nmr spectroscopy. The cyanide is then mixed with 1.3 moles of methylene bromide and added into a 50% aqueous solution of sodium hydroxide with either tetraethylammonium bromide or benzyl triethyl ammonium chloride as catalyst. The reaction mixture is heated to reflux (90°) for three hours until 95% of the starting material consumed. There is always about 5% of α-n-butyl 2,4-dichlorobenzyl cyanide remain unreacted in this reaction.

B. 1-[2-Cyano-2-(2,4-dichlorophenyl)hexyl]-1,2,4-triazole

To a dimethyl sulfoxide solution (25 ml) of sodium 1,2,4-triazole, generated from 3.2 g (0.046 m) of 1H-1,2,4-triazole and 1.85 g (0.046 m) of sodium hydroxide, is added 2-cyano-2-(2,4-dichlorophenyl) hexyl bromide dropwise at 110°. The whole is stirred at 110° for 1½ hours. The reaction mixture is poured into 400 ml of water and extracted with ether. The combined ether extracts are washed with water and dried over MgSO$_4$. Drying agent was filtered and to the filtrate is added conc. nitric acid dropwise until no more precipitates form. The precipitate (8.0 g) is filtered and is characterized as the nitric acid salt (RH 45,136) of the desired product.

nmr (DMSO): δ0.6–2.5 (complex multiplets, 9H, 5.2 (q, 2H), 7.5–7.9 (m, 3H), 8.3 (s, 1H), 8.7 (s, 1H), 14.7 (s, 1H).

EXAMPLE 4

The free base is obtained when the above nitrate salt is back neutralized with 10% ammonium hydroxide solution.

nmr (CDCl$_3$): δ0.7–2.8 (complex multiplets, 9H), 5.0 (q, 2H), 7.1–7.6 (m, 3H), 7.9 (s, 1H), 8.0 (s, 1H).

EXAMPLE 9

Zinc chloride complex of 1-[2-cyano-2-phenylhexyl]-1,2,4-triazole

To 6.5 g (0.0256 mole) of 1-[2-cyano-2-phenylhexyl]-1,2,4-triazole in 120 ml of methanol is added 1.5 g (0.0111 mole) of zinc chloride and let stir for 15 minutes. The methanol is stripped to give 9.6 g of residue. This material is taken up in warm ethanol, and the solid product precipitates. The material is separated by filtration to give 5.9 g (59%) of the product, mp 175°–177°.

EXAMPLE 11

1-[2-Cyano-2-(2,4-dichlorophenyl)decyl]-1,2,4-triazole

To 7.0 g (0.07697 mole) of the sodium salt of 1H-1,2,4-triazole, generated from 5.3 g; (0.07697 mole) of 1H-1,2,4-triazole and 3.1 g (0.759 mole) of NaOH, in 50 ml of DMSO, is added 30.0 g (0.0767 mole) of 2-cyano-2-(2,4-dichlorophenyl) decyl bromide (prepared by the usual route); and the reaction is stirred at 130° for 20 hours. The mixture is then cooled and mixed with 200 ml of water. The organic material which separates is extracted 2×100 ml of ether, and the extract is washed 2×50 ml of water, dried over anhydrous magnesium sulfate and concentrated to give 24.0 g (82.5%) of the crude product. This material is dissolved in ether, and it is treated with hydrogen chloride gas until it is acidic to litmus. The solid which precipitates is separated by filtration to give 9.0 g (28.2%) of the hydrochloric salt, mp 125°–31°. To 6.7 g (0.0161 mole) of the hydrochloride salt in 200 ml of water is stirred. The organic soluble material is extracted 2×200 ml of ether, and the extract is washed 2×50 ml of water, dried over anhydrous magnesium sulfate, and concentrated to give 4.9 g (80.2%) of the oil product.

In TABLE I, the structures of the above-identified representative compounds of this invention and of additional representative compounds of this invention prepared by the methods described above are set forth. In TABLE II, the melting points and elemental analyses of Examples 1–18 are provided.

TABLE I $$Z-\underset{R}{\underset{|}{\overset{CN}{\underset{|}{C}}}}-CH_2-Q.Y$$

| Example No. | Z | R | Q | Y |
|---|---|---|---|---|
| 1 | 2,4-ClC$_6$H$_3$ | C$_4$H$_{9n}$ | 4-triazole | — |
| 2 | 2,4-ClC$_6$H$_3$ | C$_4$H$_{9n}$ | 1&4-triazole | HNO$_3$ |
| 3 | 2,4-ClC$_6$H$_3$ | C$_4$H$_{9n}$ | 1-triazole | HNO$_3$ |
| 4 | 2,4-ClC$_6$H$_3$ | C$_4$H$_{9n}$ | 1-triazole | — |
| 5 | 4-ClC$_6$H$_4$ | CH$_3$ | 1-triazole | — |
| 6 | 4-ClC$_6$H$_4$ | CH$_3$ | 1-triazole | HNO$_3$ |
| 7 | C$_6$H$_5$ | C$_4$H$_{9n}$ | 1-triazole | HCl |
| 8 | C$_6$H$_5$ | C$_4$H$_{9n}$ | 1-triazole | — |
| 9 | C$_6$H$_5$ | C$_4$H$_{9n}$ | 1-triazole | ½ZnCl$_2$ |
| 10 | 2,4-ClC$_6$H$_3$ | C$_8$H$_{17}$ | 1-triazole | HCl |
| 11 | 2,4-ClC$_6$H$_3$ | C$_8$H$_{17}$ | 1-triazole | — |
| 12 | 2,4-ClC$_6$H$_3$ | CH$_2$CH=CH$_2$ | 1-triazole | — |
| 13 | C$_6$H$_5$ | C$_6$H$_5$ | 1-triazole | — |
| 14 | C$_6$H$_5$ | C$_6$H$_5$ | 1-triazole | HCl |
| 15 | C$_6$H$_5$ | 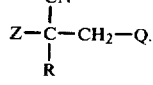 | 1-triazole | — |
| 16 | C$_6$H$_5$ | 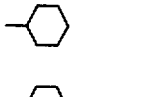 | 1-triazole | HNO$_3$ |
| 17 | C$_6$H$_5$ | CH$_2$C$_6$H$_5$ | 1-triazole | — |
| 18 | C$_6$H$_5$ | CH$_2$C$_6$H$_5$ | 1-triazole | HNO$_3$ |

TABLE II

| Example No. | mp °C. | Elemental Analysis: Calc'd (found) | | | | |
|---|---|---|---|---|---|---|
| | | C | H | Cl | N | O or Zn |
| 1 | 46–9 | 55.74 (55.40) | 4.99 (5.12) | 21.94 (21.82) | 17.33 (17.18) | |
| 2 | 110–120 | 46.65 | 4.44 | 18.36 | 18.13 | 12.43 |

TABLE II-continued

| Example No. | mp °C. | Elemental Analysis: Calc'd (found) | | | | |
|---|---|---|---|---|---|---|
| | | C | H | Cl | N | O or Zn |
| | | (46.41) | (4.30) | (18.55) | (18.36) | (12.77) |
| 3 | 156–8 | 46.65 | 4.41 | 18.36 | 18.13 | 12.43 |
| | | (46.30) | (4.61) | (18.50) | (18.27) | (12.54) |
| 4 | oil | 55.74 | 4.99 | 21.94 | 17.33 | |
| | | (55.91) | (5.09) | (22.07) | (17.21) | |
| 5 | 114–6 | 58.43 | 4.49 | 14.37 | 22.71 | |
| | | (57.40) | (5.03) | (13.37) | (19.48) | |
| 6 | 163(dec.) | 46.54 | 3.90 | 11.45 | 22.61 | 15.50 |
| | | (47.28) | (3.90) | (11.50) | (21.97) | (16.00) |
| 7 | 162–65 | 61.95 | 6.59 | 12.19 | 19.27 | |
| | | (61.10) | (6.35) | (10.49) | (17.91) | |
| 8 | oil | 70.84 | 7.13 | — | 22.03 | |
| | | (71.36) | (7.19) | | (20.82) | |
| 9 | 175–77 | 55.87 | 5.60 | 10.99 | 17.37 | 10.13 |
| | | (56.10) | (5.70) | (12.05) | (17.01) | (9.04) |
| 10 | 125–31 | 54.88 | 6.60 | 25.58 | 13.48 | |
| | | (54.80) | (5.95) | (24.77) | (13.76) | |
| 11 | oil | 60.16 | 6.37 | 18.70 | 14.77 | |
| | | (56.97) | (6.48) | (17.93) | (14.25) | |
| 12 | 88–90 | 54.74 | 3.94 | 23.08 | 18.24 | |
| | | (54.97) | (3.97) | (22.85) | (18.59) | |
| 13 | 128–9 | 74.43 | 5.14 | | 20.43 | |
| | | (74.00) | (5.27) | | (19.97) | |
| 14 | 190–3 | 65.70 | 4.87 | 11.40 | 18.03 | |
| | | (64.30) | (4.69) | (11.03) | (17.78) | |
| 15 | oil | 73.09 | 6.86 | | 20.05 | |
| | | (72.58) | (7.33) | | (18.36) | |
| 16 | 92–6 | 59.64 | 5.89 | | 20.45 | 14.02 |
| | | (60.93) | (6.45) | | (18.51) | (13.84) |
| 17 | 115–8 | 74.98 | 5.59 | | 19.43 | |
| | | (75.26) | (5.61) | | (19.42) | |
| 18 | 158–161 | 61.53 | 4.88 | | 19.93 | 13.66 |
| | | (62.19) | (4.96) | | (20.04) | (13.92) |

The 1&4-arylcyanoalkyl-1,2,4-triazoles, enantiomorphs, acid addition salts and metal salt complexes of this invention are broad-spectrum fungicides which possess a high degree of activity against assorted phytopathogenic fungi. These compounds, enantiomorphs, salts and complexes are particularly effective at rates of application from about 50 to about 2000 ppm in controlling barley net blotch (*Helminthosporium teres*) on barley plants, grey mold (*Botrytis cinerea*) on faba beans, bean powdery mildew (*Erysiphe polygoni*) on bean plants, grape downy mildew (*Plasmopora viticola*) on grape seedlings, rice blast (*Piricularia oryzae*) on rice plants, tomato late blight (*Phytophthora infestans*) on tomato seedlings, and wheat stem rust (*Puccinia graminis* f. sp. *tritici* race 15B-2) on wheat seedlings.

In evaluating these compounds, a preliminary fungicidal evaluation is carried out using the compounds at 300 ppm and spraying the plants to run off in a carrier volume of about 150 gallons/acre.

The general procedure is to take potted plants in proper condition of growth for susceptibility to the fungal disease to be evaluated, to spray these on a moving belt and allow them to dry. The proper plants are then inoculated with the fungal spores and then allowed to incubate until the disease has developed and the percent control is read or estimated.

The following test methods are employed in evaluating the fungicidal activity of the compounds, enantiomorphs, salts and complexes of this invention.

EXAMPLE A

Barley Net Blotch (*Helminthosporium teres*)

Barley plants (var. Wong) are trimmed to a height of approximately 2.5 inches, 24 hours prior to chemical application. This procedure provides plants of a uniform height and permits rapid inoculation of treated plants. The barley plants are inoculated by spraying the foliage of the plants with a hand sprayer until small droplets of the inoculum are observed on the leaves. Inoculated plants are incubated in a humid environment at 75°-80° F. for 24 hours prior to being placed in the greenhouse at 70°-75° F. Treatment comparisons are made 6 to 7 days after inoculation. Typical barley net blotch symptoms initially appear as irregular sunken water-soaked areas which become necrotic as the lesions enlarge. Certain of the 1&4-arylcyanoalkyl-1,2,4-triazoles of this invention demonstrate complete control over *Helminthosporium teres* at application rates of 300 ppm.

EXAMPLE B

Broad Bean Gray Mold Leaf Spot (*Botrytis cinerea*)

Broad bean plants (var. Vicia faba) are trimmed to a height of approximately 4.5 inches, 24 hours prior to chemical application. This procedure provides plants of a uniform height and permits rapid and uniform inoculation of the treated plants. Broad bean plants are inoculated by spraying the foliage with a herbicide belt sprayer. Inoculated plants are incubated in a humid environment at 75°-80° F. for 66 hours. Treatment comparisons are made 66 to 68 hours after inoculation. Typical broad bean gray mold leaf spot symptoms appear as regular circular to lanceolate lesions on plant leaves and stems. Certain of the 1&4-arylcyanoalkyl-1,2,4-triazoles of this invention demonstrate greater than 70% control over *Botrytis cinerea* at application rates of 300 ppm.

EXAMPLE C

Bean Powdery Mildew (*Erysiphe polygoni*)

Bean plants (var. Drawf Hort) are thinned to two plants per pot 24 hours prior to chemical application. Bean plants are inoculated by spraying the leaves and stems with inoculum until a uniform film of inoculum is observed on the plant. Inoculated plants are maintained under existing greenhouse conditions. Treatment comparisons are made 8 to 10 days after inoculation. Typical bean powdery mildew symptoms are circular white mycelial mats (fructifications) on the leaf surface. The majority of the 1&4-arylcyanoalkyl-1,2,4-triazoles of this invention demonstrate complete control over *Erysiphe polygoni* at application rates greater than 300 ppm.

EXAMPLE D

Grape Downy Mildew (*Plasmopora viticola*)

Grape seedlings (var. Siebel 1000) 4 to 5 inches tall are used. *Plasmopora viticola* is cultured on grape leaves for 7 days at 65°-75° F. The grape plants are inoculated by spraying the leaves with a hand held air brush until small uniform droplets of inoculum are observed on the leaves. The inoculated plants are incubated in a humid environment at 65°-70° F. for 48 hours prior to being placed in a growth room. Typical grape downy mildew symptoms appear on the upper surface as pale-yellow spots variable in size and form, frequently circular without a distinct line of demarcation. Under humid conditions the lower leaf surface is covered by conspicuous fungal growth. Certain of the 1&4-arylcyanoalkyl-1,2,4-triazoles of this invention possess greater than 90% control over *Plasmopora viticola* at application rates of 300 ppm.

EXAMPLE E

Rice Blast (*Piricularia oryzae*)

Rice plants (var. Nova 66) are trimmed to a height of approximately 5 inches, 24 hours prior to chemical application. This procedure provides plants of uniform height and permits rapid inoculation of treated plants. Rice plants are inoculated by spraying the leaves and stems with an air brush until a uniform film of inoculum is observed on the leaves. The inoculated plants are incubated in a humid environment (75°–80° F.) for 24 hours prior to be placed in a greenhouse environment. Treatment comparisons are made 7 to 8 days after inoculation. Initial rice blast lesions appear as small brown necrotic spots on the foliage. The typical lesion is ecliptical, 1 to 2 cm. long with a large necrotic gray center and brown margins. Certain of the 1-arylcyanoalkyl-1,2,4-triazoles of this invention possess complete control over *Piricularia oryzae* at application rates of 300 ppm.

EXAMPLE F

Tomato Late Blight (*Phytophthora infestans*)

Tomato (var. Rutgers) seedlings, 2.5 to 3 inches tall, are fertilized with a water soluble fertilizer 4 to 5 days prior to chemical application to promote rapid succulent growth and better symptom expression. The spore suspension is applied with a DeVilbiss atomizer at 8 to 10 psi. air pressure onto the leaf undersurface until fine droplets are formed. Inoculated seedlings are placed in a humid environment at 60°–62° F. for 40 to 45 hours, prior to being placed in the greenhouse at 70°–75° F. Treatment comparisons are made 5 to 6 days after inoculation. Initially, typical tomato late blight symptoms appear as irregular, greenish-black, water-soaked patches which enlarge and become brown, with a firm corrugated surface. Severe infection will resemble frost damage. Certain of the 1-arylcyanoalkyl-1,2,4-triazoles of the present invention possess complete control over *Phytophthora infestans* at application rates of 300 ppm.

EXAMPLE G

Wheat Stem Rust (*Puccinia graminis* f. sp. *tritici* race 15B-2)

Seven-day-old wheat plants (var. Monon) are trimmed to approximately 2.5 inches, 24 hours prior to chemical application to provide a uniform plant height and to facilitate uniform inoculation. Wheat stem rust is cultured on wheat seedlings (var. Monon) for a period of 14 days under existing greenhouse conditions. Wheat plants are inoculated by applying the stem rust spore suspension, until run-off, with a DeVilbiss atomizer at 5 psi. air pressure. After inoculation, the plants are placed into a humid environment at approximately 68° F. A timer is used to permit 12 hours of continuous darkness followed by a minimum of 3 to 4 hours of light with an intensity of 500 foot candles. The temperature in the chamber should not exceed 85° F. At the end of the light period, the fogger is turned off and vented to allow the plants to dry slowly prior to being placed into a greenhouse environment. The plants are permitted to grow under greenhouse conditions for a period of 2 weeks prior to making treatment comparisons. Wheat stem rust is characterized by brick red spores in irregularly shaped sori on the leaves and stems of the wheat seedlings. Certain of the 1&4-arylcyanoalkyl-1,2,4-triazoles of the present invention possess complete control over *Puccinia graminis* f. sp. *tritici* race 15B-2 at application rates of 300 ppm.

The following examples, H-M, illustrate the fungicidal activity of the 1- and 4-arylcyanoalkyl-1,2,4-triazoles of this invention compared with that of the arylcyanoalkylimidazoles disclosed in U.S. Pat. No. 4,073,921 issued Feb. 14, 1978.

The experimental compounds are designated as follows:

I = 1-[2-cyano-2-(phenyl)hexyl]-1,2,4-triazole (Example No. 8 of this invention)

II = 1-[2-cyano-2-(phenyl)hexyl]-imidazole (Example No. 1 of U.S. Pat. No. 4,073,921)

III = 1-[2-cyano-2-(2,4-dichlorophenyl)hexyl]-1,2,4-triazole (Example No. 4 of this invention)

IV = 1-[2-cyano-2-(2,4-dichlorophenyl)hexyl]-imidazole (Example No. 14 of U.S. Pat. No. 4,073,921).

EXAMPLES H and I

Comparative Wheat Leaf Rust and Wheat Stem Rust by Seed Treatment

Examples H and I illustrate the residual activity of a representative triazole of this invention with that of a representative imidazole of U.S. Pat. No. 4,073,921 for the control of wheat leaf rust and wheat stem rust by means of wheat seed treatment.

Twenty (20) gram aliquots of wheat (var. Wanser) seed were slurry treated by pipetting 2 ml of the experimental compound, dissolved in an acetone:methanol (1:1) solution, onto the seed contained in a 2-ounce wide-mouth jar. The amounts of experimental compound used are equivalent to use rates of 0.5, 1.0, 2.0, and 4.0 ounces of active ingredient (ai) per 100 pounds of seed. The jar was then shaken vigorously to allow thorough seed coverage and the damp seed was then spread on aluminum foil squares and permitted to air-dry.

The treated wheat seed was planted in 3-inch plastic greenhouse pots containing autoclaved soil. Six pots were planted for each compound use rate. Two weeks after planting, three pots were inoculated with wheat leaf rust (*Puccinia recondita*) and three pots with wheat stem rust (*Puccinia graminis* f. sp. *tritici* race 15B) as follows:

EXAMPLE H

A spore suspension of *Puccinia recondita* is prepared by placing wheat leaf rust infected wheat leaves into a pint jar and adding water and the surfactant TWEEN-80[R] (1 drop/100 cc). The surfactant serves to free the rust urediospores from the sori and improves inoculum distribution on the wheat foliage. The resulting spore suspension is filtered through cheesecloth to remove leaf debris and the resulting spore suspension adjusted to a concentration of $2\times10^4$ spores per ml.

Wheat seedlings are inoculated by applying the wheat leaf rust spore suspension, until run-off, with a DeVilbiss atomizer at 5 psi air pressure. The inoculated plants are placed into a humidity cabinet for 24 hr. at a temperature of 70°-75° F. and a relative humidity of 98-99%. After the incubation period, the inoculated seedlings are maintained under greenhouse conditions. The results are reported in Table III below.

Table III shows that the representative triazole compound provides 99-100% disease control by seed treatment at application rates as low as 1 oz ai/cwt seed for 35 days whereas treatment at a rate of 4 oz ai/cwt seed of the representative imidazole provides only 70–89% disease control for 21 days and less than 50% disease control for 35 days.

EXAMPLE I

A spore suspension of *Puccinia graminis* f. sp. *tritici* race 15B-2 is made by excising infected wheat leaves and placing the leaves into a pint jar containing water and the surfactant "Tween 80" (1 drop/100 cc). The surfactant serves to free the rust slurediospores from the sori and improves inoculum retention when applied to plant foilage. The resulting spore suspension is filtered through cheesecloth to remove the leaves and assorted other plant debris. The spore concentration is not adjusted, but a minimum of $2.5\times10^4$ spores per mil are required to obtain an acceptable disease level.

Wheat plants are inoculated by applying the stem rust spore suspension until run-off, with a DeVilbiss atomizer at 5 psi air pressure. After inoculation, the plants are placed into a humid environment at approximately 68° F. A timer is used to permit 12 hours of continuous darkness followed by a minimum of 3-4 hours of light with an intensity of 500 ft. candles. The temperature in the chamber is not permitted to exceed 85° F. At the end of the light period, the fogger is turned off and vented to allow the plants to dry slowly prior to being placed into a greenhouse environment. The results are reported in Table IV below.

Table IV shows that the representative triazole provided 97-100% disease control at an application rate as low as 0.5 oz. ai/cwt seed for 42 days whereas the representative imidazole provides only 70-89% disease control for 28 days and less than 50% disease control for 42 days at an application rate of 4 oz. ai/cwt seed.

TABLE III

Comparative Residual Activity: Wheat (var. Wanser) Seed Treatments for Foliar leaf Rust (*Puccinia recondita*) Control

| Compound | oz.ai/cwt wheat seed | Foliar Disease Control Level[a,b] (days after treatment) 21 | 35 |
|---|---|---|---|
| I | 0.5 | A | E |
| | 1.0 | A | A |
| | 2.0 | A | A |
| | 4.0 | A | A |
| II | 0.5 | E | E |
| | 1.0 | E | E |
| | 2.0 | E | E |
| | 4.0 | C | E |
| Control | — | E | E |

[a]Disease Control Level. A = 97-100%, B = 90-96%, C = 70-89%, D = 50-69%, E = less than 50% disease control.
[b]Average reading for 3 replicates

TABLE IV

Comparative Residual Activity: Wheat (var. Wanser) Seed Treatments for Foliar Wheat Stem rust (*Puccinia graminis* f. sp. tritici race 15B) Control

| Compound | oz. ai/cwt Wheat seed | Foliar Disease Control Level[a,b] (days after treatment) 28 | 42 |
|---|---|---|---|
| I | 0.5 | A | A |
| | 1.0 | A | A |
| | 2.0 | A | A |
| | 4.0 | A | A |
| II | 0.5 | E | E |
| | 1.0 | E | E |
| | 2.0 | E | E |
| | 4.0 | C | E |

TABLE IV-continued

Comparative Residual Activity: Wheat (var. Wanser) Seed Treatments for Foliar Wheat Stem rust (*Puccinia graminis* f. sp. tritici race 15B) Control

| Compound | oz. ai/cwt Wheat seed | Foliar Disease Control Level[a,b] (days after treatment) 28 | 42 |
|---|---|---|---|
| Control | — | E | E |

[a]Disease Control Level-A = 97-100%, B = 90-96%, C = 70-89%, D = 50-69%, E = less than 50% disease control.
[b]Average reading for 3 replicates.

EXAMPLE J

Comparative Squash Powdery Mildew Control by Foliar Application

This example compares the fungicidal activity, determined in field tests, against Squash Powdery Mildew of a representative triazole compound according to the invention with that of a representative imidazole of U.S. Pat. No. 4,073,921 by foliar application.

The experimental compounds were spray applied at a rate of from 0.06 to 0.25 lb. ai/100 gal in an acetone in water (1:4) solution to squash plants (var. G. Crookneck) about 5 weeks after field planting, the squash plants being naturally infected with powdery mildew (*Erysiphe cichoracearm*). The experimental compounds were applied to one set of plants on a 10-day spray schedule designated "A", and to a second set of plants on a 20-day spray schedule designated "B". The results were observed 20 days and 30 days after initial treatment.

Table V shows that both experimental compounds provided similar levels of control of squash powdery mildew control when applied on a 10-day spray schedule at each level of foliar treatment. However, when applied on a 20-day spray schedule, the highest level of residual activity was attained by the representative triazole. Also, the representative triazole applied at a rate of 0.06 lb. ai/100 gal was approximately as effective as the representative imidazole applied at the higher rate of 0.25 lb. ai/100 gal.

TABLE V

Comparative Squash (var. Grookneck) Powdery Mildew (*Erysiphe cichoracearum*) Control by: Foliar Applications

| Compound | Rate (lb. ai/100 gal.) | Spray Schedule[a] | % Powdery Mildew Control days after treatment 20 | 30 |
|---|---|---|---|---|
| I | 0.06 | A | 93 | 96 |
| | 0.125 | A | 100 | 100 |
| | 0.25 | A | 100 | 100 |
| | 0.06 | B | 76 | 76 |
| | 0.125 | B | 76 | 86 |
| | 0.25 | B | 85 | 88 |
| II | 0.06 | A | 100 | 98 |
| | 0.125 | A | 100 | 98 |
| | 0.25 | A | 100 | 98 |
| | 0.06 | B | 12 | 28 |
| | 0.125 | B | 52 | 32 |
| | 0.25 | B | 71 | 72 |

[a]A = 10 days between spray cycles; B = 20 days between spray cycles.
[b]Average percent powdery mildew infection in untreated control plots: 20 days = 42%; 30 days = 50%

EXAMPLE K

Comparative Southern Leaf Blight Control in Sweet Corn by Foliar Application This example compares, in field tests, the activity of a representative triazole according to the invention against Southern Leaf Blight (*Helminthosporium maydis*) with that of a representative imidazole of U.S. Pat. No. 4,073,921 in sweet corn by foliar application.

The experimental compounds were spray applied at a rate of from 0.125 to 0.5 lb. ai/100 gal in an acetone:water (1:4) solution to sweet corn plants (var. Asgrow X P382 N) on 7- and 14-day spray schedules beginning about 2 months after field planting, the plants being naturally infected with Southern Leaf Blight. The results were observed 3 and 4 weeks after treatment.

Table VI shows that the representative triazole provides substantially more effective control of Southern Leaf Blight in sweet corn at each application rate tested on both spray schedules.

TABLE VI

Comparative Southern leaf Blight (*Helminthosporium maydis*) Control in Sweet Corn

| Treatment | Rate (lb. ai/100 gal.) | Spray Schedule[a] | % H. Maydis Control[b] (weeks after treatment) 3 | 4 |
|---|---|---|---|---|
| I | 0.125 | A | 90 | 90 |
|   | 0.25  | A | 81 | 95 |
|   | 0.5   | A | 94 | 97 |
|   | 0.125 | B | 58 | 75 |
|   | 0.25  | B | 75 | 68 |
|   | 0.5   | B | 77 | 84 |
| II | 0.125 | A | 19 | 19 |
|   | 0.25  | A | 10 | 17 |
|   | 0.5   | A | 32 | 29 |
|   | 0.125 | B | 19 | 10 |
|   | 0.25  | B | 6  | 0  |
|   | 0.5   | B | 10 | 13 |

[a]A = 7 days between spray cycles; B = 14 days between spray cycles.
[b]Average percent southern leaf blight infection in untreated controls: 3 weeks = 62%; 4 weeks = 63%

EXAMPLE L

Comparative Wheat Powdery Mildew Control by Foliar Application

This example illustrates the comparative activity of representative triazole and imidazole compounds against wheat powdery mildew in field tests.

Wheat (var. 'Pennoll') plants were sprayed with 2, 5, 10, 19, 38, 75, 150, or 300 ppm ai of experimental compound in an acetone:methanol:water (1:1:2) solvent system. Treatments were replicated 2X. After the treated plants had dried, they were placed in a day length neutral, constant temperature room (68°) whereupon natural infection of the plants occurred. Disease control was evaluated beginning on the 17th day after treatment.

The results in Table VII show that maximal disease control was attained using the triazole at a concentration of 19 ppm ai after 17 days whereas use of the imidazole at a concentration of 75 ppm ai was required to provide maximal disease control after 17 days. Also, greater than 90% disease control was sustained by the triazole at a concentration of 75 ppm ai for 30 days whereas 300 ppm ai of the imidazole sustained a similar level of disease control for 22 days. The data tends to show that more effective wheat powdery mildew control is attained by the triazole than by the imidazole.

TABLE VII

Comparative Residual Activity: Wheat Powdery Mildew Control Treatments Replicated 2×

| Compound | Conc. (ppm ai) | Disease Control Rating[a] (days after treatment) |     |     |     |     |     |     |     |
|---|---|---|---|---|---|---|---|---|---|
|   |   | +17 | +19 | +22 | +24 | +26 | +28 | +30 | +32 |
| I | 300 | A | A | A | A | A | A | A | B |
|   | 150 | A | A | A | A | A | B | B | B |
|   | 75  | A | A | A | A | A | B | B | E |
|   | 38  | A | A | A | A | A | C | E | E |
|   | 19  | A | A | B | E | E | E | E | E |
|   | 10  | D | E | E | E | E | E | E | E |
|   | 5   | E | E | E | E | E | E | E | E |
|   | 2   | E | E | E | E | E | E | E | E |
| II | 300 | A | A | B | C | C | E | E | E |
|   | 150 | A | B | C | D | D | E | E | E |
|   | 75  | A | B | E | E | E | E | E | E |
|   | 38  | B | B | E | E | E | E | E | E |
|   | 19  | B | E | E | E | E | E | E | E |
|   | 10  | E | E | E | E | E | E | E |   |
|   | 5   | E | E | E | E | E | E | E | E |
|   | 2   | E | E | E | E | E | E | E | E |

[a]Disease Control Rating: A = 97–100%, B = 90–96%, C = 70–89%, D = 50–69%, and E = less than 50%

EXAMPLE M

Comparative Wheat Stem Rust Control by Root Uptake

This example compares the fungicidal activity of two representative triazole and imidazole compounds against Wheat Stem Rust (*Puccinia graminis* f. sp. *tritici*)

The experimental compounds were dissolved in acetone:methanol:water (1:1:44). The solutions were added to 3" pots containing 2-day old wheat (var. Wanser) seedlings. Twenty-four hours after treatment, the plants were innoculated with fresh uredispores of wheat stem rust prepared following standard procedures.

The results in Table VIII show that after 11 days maximal disease control is attained using 25 ppm and 50 ppm of triazoles I and III, respectively, whereas 200 ppm of imidazole II was required for maximal disease control. Imidazole IV applied at 200 ppm did not even attain 50% disease control.

TABLE VIII

Comparative Residual Activity: Wheat Stem Rust (*Puccinia graminis* f. sp. tritici) by root uptake

| Compound (Imidazole/Triazole) | Pounds Per Acre | Disease Control Level[a] (imidazole/triazole) | |
|---|---|---|---|
| IV/III | 200 | E | A |
|  | 100 | E | A |
|  | 50 | E | A |
|  | 25 | E | B |
| II/I | 200 | A | A |
|  | 100 | B | A |
|  | 50 | C | A |
|  | 25 | C | A |

[a] A = 97-100% disease control; B = 90-96%; C = 70-89%; D = 50-69%; E = less than 50%

The 1&4-arylcyanoalkyl-1,2,4-triazoles, enantiomorphs, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in a carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solution can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 1-[β-cyano-β-(2,4-dichlorophenyl)hexyl]1,2,4-triazole, 45 parts of a synthetic precipitated hydrated silicon dioxide sold under the trademark Hi-Sil ®, and 5 parts of sodium lignosulfonate. In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ®7.

Dusts are prepared by mixing the 1&4-arylcyanoalkyl-1,2,4-triazoles, enantiomorphs, salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The 1&4-arylcyanoalkyl-1,2,4-triazoles, enantiomorphs, salts and complexes thereof can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention includes:
 (a) dithiocarbamate and derivatives such as:
  ferric dimethyldithiocarbamate (ferbam),
  zinc dimethyldithiocarbamate (ziram), manganese ethylenebisdithiocarbamate (maneb) and its coordination product with zinc ion (mancozeb),
  zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide,
  3,5-dimethyl-1,3,5-2H-tetrahydrothiadiazine-2-thione (dazomet); and mixtures of these and mixtures with copper salts;
 (b) nitrophenol derivatives such as:
  dinitro-(1-methylheptyl) phenyl crotonate (dinocap), 2-sec-butyl-4,6-dinitrophenyl 3,3-dimethylacrylate (binapacryl), and
  2-sec-butyl-4,6-dinitrophenyl isopropyl carbonate;
 (c) heterocyclic structures such as:
  N-trichloromethylthiotetrahydrophthalimide (captan), N-trichloromethylthiophthalimide (folpet), 2-heptadecyl-2-imidazole acetate (glyodine), 2-octylisothiazol-3-one, 2,4-dichloro-6-(o-chloroanilino)-s-triazine,
  diethyl phthalimidophosphorothioate, 4-butyl-1,2,4-triazole, 5-amino-1-[bis(dimethylamino)-phosphinyl]-3-phenyl-1,2,4-triazole, 5-ethoxy-3-trichloromethyl-1,2,4-thiadiazole,
  2,3-dicyano-1,4-dithiaanthraquinone (dithianon), 2-thio-1,3-dithio-[4,5-b]quinoxaline (thioquinox) methyl 1-(butylcarbamoyl)-2-benzimidazole carbamate (benomyl), 2-(4'-thiazolyl) benzimidazole (thiabendazole), 4-(2-chlorophenylhydrazono)-3-methyl-5-isoxazolone, pyridine-2-thiol-1-oxide, 8-hydroxyquinoline sulfate and metal salts thereof;

2,3-dihydro-5-carboxanilido-6-methyl-1,4-oxathiin-4,4-dioxide, 2,3-dihydro-5-carboxanilido-6-methyl-1,4-oxathiin, α-(phenyl)-α-(2,4-dichlorophenyl)-5-pyrimidinyl-methanol (triarimol), cis-N-[(1,1,2,2-tetrachloroethyl)thio]-4-cyclohexene-1,2-dicarboxyimide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methylpyrimidine (ethirimol), acetate of 4-cyclododecyl-2,6-dimethylmorpholine (dodemorph), and 6-methyl-2-oxo-1,3-dithiolo[4,5-b]quinoxaline (quinomethionate).

(d) miscellaneous halogenated fungicides such as:
tetrachloro-p-benzoquinone (chloranil),
2,3-dichloro-1,4-naphthoquinone (dichlone),
1,4-dichloro-2,5-dimethoxybenzene (chloroneb),
3,5,6-trichloro-o-anisic acid (tricamba),
2,4,5,6-tetrachloroisophthalonitrile (TCPN),
2,6-dichloro-4-nitroaniline (dichloran),
2-chloro-1-nitropropane,
polychloronitrobenzenes such as:
pentachloronitrobenzene (PCNB) and
tetrafluorodichloroacetone;

(e) fungicidal antibiotics such as:
griseofulvin, kasugamycin and streptomycin;

(f) copper-based fungicides such as:
cuprous oxide, basic cupric chloride, basic copper carbonate, copper naphthenate, and Bordeaux mixture; and (g) miscellaneous fungicides such as:
diphenyl, dodecylguanidine acetate (dodine), phenylmercuric acetate, N-ethylmercuri-1,2,3,6-tetrahydro-3,6-endomethano-3,4,5,6,7,7,-hexachlorophthalimide,
phenylmercuric monoethanol ammonium lactate,
p-dimethylaminobenzenediazo sodium sulfonate,
methyl isothiocyanate, 1-thiocyano-2,4-dinitrobenzene, 1-phenylthiosemicarbazide,
nickel-containing compounds, calcium cyanamide, lime sulfur, sulfur, and 1,2-bis(3-methoxycarbonyl-2-thioureido) benzene (thiophanatemethyl).

The 1&4-arylcyanoalkyl-1,2,4-triazoles, enantiomorphs, acid addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the 1&4-arylcyanoalkyl-1,24-triazoles of this invention will suggest themselves to those skilled in the art of agriculture and horticulture.

We claim:

1. A compound of the formula

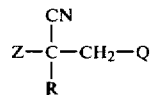

wherein
Z is unsubstituted phenyl, or phenyl substituted with up to three substituents selected from the group consisting of halogen, nitro, trihalomethyl, cyano, $(C_1-C_4)$alkyl, $(C_1-C_4)$alkoxy, $(C_1-C_4)$alkylthio, $(C_1-C_4)$alkylsulfinyl and $(C_1-C_4)$alkylsulfonyl,
R is selected from the group consisting of $(C_1-C_{12})$alkyl, $(C_5-C_7)$cycloalkyl, $(C_2-C_4)$alkenyl, $(C_5-C_6)$cycloalkenyl, $(C_2-C_4)$alkynyl, unsubstituted phenyl, benzyl or phenethyl, or phenyl, benzyl or phenethyl substituted with up to two halogen atoms;
Q is an unsubstituted 1- or 4-(1,2,4-triazole)
and the agronomically acceptable enantiomorphs, acid addition salts and metal salt complexes thereof.

2. A compound according to claim 1 wherein Z is phenyl, or phenyl substituted with up to two substituents selected from the group consisting of chlorine, bromine, methyl, methoxy, nitro and methylthio; R is $(C_1$ to $C_{12})$ alkyl, cyclohexyl, allyl, cyclohexenyl, propargyl, phenyl, benzyl or phenethyl, or monochloro substituted phenyl, benzyl or phenethyl.

3. A compound according to claim 2 wherein Z is phenyl, or phenyl substituted with up to two substituents selected from the group consisting of chlorine and methyl and R is $(C_1$ to $C_8)$ alkyl or allyl.

4. A compound according to claim 3 wherein Z is 2,4-dichlorophenyl, R is $CH_3$, n—$C_4H_9$, n—$C_8H_{17}$ or allyl; Q is 1-(1,2,4-triazolyl); and the agronomically acceptable enantimorphs, and acid addition salts thereof.

5. A compound according to claim 3 wherein Z is phenyl; R is n—$C_4H_9$; Q is 1-(1,2,4,-triazolyl); and the agronomically acceptable acid addition salts thereof.

6. A fungicidal composition for controlling phytopathogenic fungi which comprises, an agronomically acceptable carrier and as the active ingredient, a fungicidally effective amount of a compound according to claim 2.

7. A fungicidal composition for controlling phytopathogenic fungi which comprises, an agronomically acceptable carrier and as the active ingredient, a fungicidally effective amount of a compound according to claim 5.

8. A method for controlling phytopathogenic fungi which consists of applying to a plant, to plant seed or to the plant habitat, a fungicidally effective amount of a compound according to claim 2.

9. A method for controlling phytopathogenic fungi which consists of applying to a plant, to plant seed or to the plant habitat, a fungicidally effective amount of a compound according to claim 5.

10. A compound according to claim 1 wherein Z is phenyl, or phenyl substituted with up to two substituents selected from the group consisting of chlorine, fluorine and methoxy, R is $(C_1$ to $C_8)$ alkyl or allyl and Q is 1-(1,2,4-triazolyl).

* * * * *